United States Patent [19]

MacFadden

[11] 4,209,590
[45] Jun. 24, 1980

[54] CELLULOSE FERMENTATION PROCESS

[75] Inventor: Donald L. MacFadden, Bristol, Tenn.

[73] Assignee: Chevron Research Company, San Francisco, Calif.

[21] Appl. No.: 916,435

[22] Filed: Jun. 19, 1978

[51] Int. Cl.² .................................................. C12B 1/00
[52] U.S. Cl. ..................................... 435/244; 435/105; 435/252; 426/53; 435/804; 435/822
[58] Field of Search ..................... 195/33, 114; 426/2, 426/53, 807; 435/105, 244, 252

[56] References Cited

U.S. PATENT DOCUMENTS 4,110,475   8/1978   Singer .............................. 195/114 X

OTHER PUBLICATIONS

Dowe et al, Journal of Animal Science, vol. 16, pp. 93 to 99 (1957).

*Primary Examiner*—Lionel M. Shapiro
*Attorney, Agent, or Firm*—D. A. Newell; T. G. DeJonghe; R. J. Suyat

[57] ABSTRACT

Cellulose fermentation by cellulose-digesting microorganisms is increased by conducting the fermentation in the presence of a minor amount of a compound of the formula

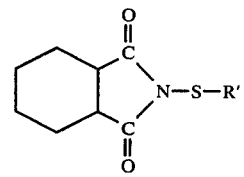

wherein R' is haloalkyl and the carbocyclic ring has from 0 to 3 sites of olefinic unsaturation.

6 Claims, No Drawings

CELLULOSE FERMENTATION PROCESS

BACKGROUND OF THE INVENTION

The effect of chemical additives in microorganism fermentations has been extensively studied. For example, P. P. Williams et al, App. Microbiology, 11, 517 (1963) describe rumen bacterial and protozoal responses to insecticide substrate; J. J. O'Connor et al, J. Animal Sci., 33, 662 (1971) describe the in vivo effect of chemical additives on production of volatile fatty acids by rumen microorganisms; L. W. Varner et al, J. Animal Sci., 33, 1110 (1971), describe the influence of ammonium salts upon rumen fermentation by steers; and T. W. Dowe et al, J. Animal Sci., 16 93 (1957) describe the effect of corn treated with fungicides (N-trichloromethylthio-delta$^4$-tetrahydrophthalimide) upon the performance of fattening steers.

DESCRIPTION OF THE INVENTION

The cellulose-fermentation-accelerating compounds of the invention are represented by the formula

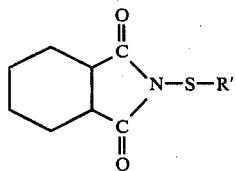

(I)

wherein R' is haloalkyl of 1 to 2 carbon atoms and 1 to 5 chloro or bromo groups and the carbocyclic ring has from 0 to 3 sites of olefinic unsaturation, i.e., 1,2-phenylene, 1,2-dihydrophenylene, 1,2-tetrahydrophenylene and hexahydrophenylene (cyclohexylene). Preferred compounds of Formula (I) are those wherein R' is chloromethyl or chloroethyl of 1 to 5 chloro groups, especially trichloromethyl or tetrachloroethyl. The compounds of Formula (I) can be considered as a phthalimide, dihydrophthalimide, tetrahydrophthalimide or hexahydrophthalimide derivative.

Representative compounds of Formula (I) are:
N-trichloromethylthiophthalimide
N-trichloromethylthio-delta$^2$,delta$^4$-dihydrophthalimide
N-tribromomethylthio-delta$^1$,delta$^3$-dihydrophthalimide
N-trichloromethylthio-delta$^2$-tetrahydrophthalimide
N-trichloromethylthio-delta$^4$-tetrahydrophthalimide
N-1,2,2,2-tetrachloroethylthiophthalimide
N-1,1,2,2-tetrachloroethylthiophthalimide
N-1,1,2,2-tetrachloroethylthio-delta$^2$,delta$^4$-dihydrophthalimide
N-pentabromoethylthio-delta$^4$-tetrahydrophthalimide
N-pentachloroethylthio-delta$^4$-tetrahydrophthalimide, and
N-1,1,2,2-tetrachloroethylthio-delta$^4$-tetrahydrophthalimide.

The amount of compound employed in the process of application depends in part upon the type of cellulosic material and the particular microorganism(s) employed. Generally, weight ratios of compounds to cellulosic matter in the range of about 1:10 to 1:1,000,000 are effective, although weight ratios in the range of about 1:100 to 1:10,000 are preferred.

In in vitro cellulose fermentation processes, the compound is generally added directly to the fermentation process. In in vivo cellulose digestion, the compound may be orally administered to the animal along with the cellulosic feedstuff. Alternatively, the cellulosic feedstuff may be pretreated with an effective amount of the compound prior to feeding the animal.

The process of the invention is generally applicable to in vivo or in vitro cellulose fermentation by microorganisms. Examples of in vitro cellulose fermentation by microorganisms are the aerobic and/or anaerobic destruction of cellulosic wastes in sewage plants; conversion of cellulose to sugar by microorganisms such as Trichoderma viride; conversion to cellulose to single-cell proteins by microorganisms such as Bacteroidaceae, Cellulomonas and Alcaliginis; and the biodegradation of lignin-cellulosic plant material. Examples of in vivo fermentation by microorganisms are cellulosic digestion by rumen microorganisms of ruminant animals, cecum microorganisms of animal intestines, and other cellulolytic organisms in the alimentary tracts of herbivores.

The process of the invention is suitably employed for all types of cellulosic material such as paper, municipal waste and plant products, e.g., wood, cotton, straw, bagasse, rice hulls, etc.

The process of the invention is particularly useful for increasing the fermentation rate of cellulose by rumen microorganisms and for increasing the fermentation rate of cellulosic waste products by sewage microorganisms. Microorganisms commonly present in sewage sludge of sewage treatment plants include anaerobic and aerobic bacteria such as Escherichia coli, Lactobacillus fermentans, Acetobacter viscosus, Acinetobnacter calcoaceticus, Actinobacillus sp., Alcaligenes eutrophus, Brevibacterium ammoniagenes, Bacillus subtilis, Celevibrio gilvus, Pseudomonas viscosa, Cellutomonas sp., Bacillus polymyxa, Streptococcus haemolyticus, Cellulomonas flavigina, Colostridium thermocellum, and Streptococcus sp.

EXAMPLES

Example 1—Cotton digestion by Bacteroides succinogenes

The organism Bacteriodes succinogenes was obtained from the American Type Culture Collection, No. 19169.
Nutrient Source:

| Bacto-fluid Thioglycolate (29 g of formulation/liter of H$_2$O | |
|---|---|
| Pancreatic Digest of Casein (Bacto-Casitone) | 15.0 g |
| Water-Soluble Portion of Autolyzed Fresh Yeast (Bacto-Yeast Extract) | 5.0 g |
| Dextrose | 5.0 g |
| NaCl | 2.5 g |
| 1-Cystine | 0.5 g |
| Thioglycolic Acid | 0.3 ml |
| Agar-Agar | 0.75 g |
| 7-Hydroxy-3H-phenoxazin-3-one-10-oxide (Rezazurin) | 0.001 g |

The rate of cotton digestion in the presence of several test compounds in the above nutrient broth with Bacteroides succinogenes was determined by the following procedure:

Cotton (100 mg) was placed in screw-cap tubes. To these the test compound (1 microgram) and the nutrient source (20 ml) were added to completely fill the tube.

The tubes were then sterilized, cooled and inoculated with the microbe (1 loop of inoculation needle), their caps tightened, and incubated in a water bath at about 40° C.

The tubes were stirred throughout incubation and the caps loosened every 2 hours for the first 18 hours and every 6 hours thereafter to release gases produced by the fermentation. After 70 hours of incubation, most of the fermentation processes had subsided, as noted by cessation of gas accumulation.

After various periods of incubation, the tubes were emptied on previously weighed filter paper. The filter paper was washed several times and dried to a constant weight. The weight of the undigested cotton was determined by difference.

TABLE I

| Time | Cotton Digestion (in mg.) | | |
|---|---|---|---|
| | Test Compound | | |
| (hr) | Control | A | B |
| 10 | 0 | 0 | 0 |
| 20 | 0.5 | 1.3 | 1.0 |
| 30 | 1.5 | 4.0 | 3.0 |
| 40 | 3.5 | 17.0 | 11.0 |
| 50 | 16.0 | 30.0 | 23.0 |
| 60 | 30.0 | 40.0 | 35.0 |
| 70 | 37.5 | 44.0 | 42.0 |

A = N-(trichloromethylthio)-delta$^4$-tetrahydrophthalimide
B = N-(1,1,2,2-tetrachloroethylthio)-delta$^4$-tetrahydrophthalimide EXAMPLE 2—Cotton digestion by *Bacteriodes succinogenes*

The rate of cotton digestion with *Bacteroides succinogenes* in the presence of several test compounds was determined by a procedure similar to that of Example 1, except that the incubation period was 8 days and no stirring was employed. The test compounds and the results are tabulated in Table II.

TABLE II

| Concentration | Total mg Cellulose Digested | | |
|---|---|---|---|
| | Test Compound | | |
| (micrograms) | A | B | C |
| 0 (control) | 80 | 90 | 105 |
| 1 | 115.0 | 112.5 | 122.5 |
| 100 | 142.5 | 115.0 | 132.5 |
| 400 | 135.0 | 117.5 | 137.5 |

A and B = as in Table I
C = N-trichloromethylthiophthalimide

EXAMPLE 3—Plant cellulose digestion by *Bacteroides succinogenes*

Lignin-cellulosic matter of herbaceous plant forage was digested by *Bacteroides succinogenes* in a purified medium in the presence of N-(trichloromethylthio)-delta$^4$-tetrahydrophthalimide (Captan) at a concentration of 10 micrograms/ml by a procedure identical to that of Example 1.

The results are tabulated in Table III.

Table III

| Incubation | Cellulose Digestion, % | |
|---|---|---|
| | Treatment | |
| Time, hrs. | Control | Captan |
| 9 | 1.5 | 2.0 |
| 12 | 2.0 | 3.0 |
| 15 | 3.0 | 7.5 |
| 18 | 7.5 | 20.0 |
| 21 | 21.0 | 38.0 |
| 24 | 32.5 | 44.0 |
| 48 | 37.5 | 45.0 |

This example exemplifies the in vitro separation of cellulose from lignin-cellulosic matter by biodegradation of the cellulose.

EXAMPLE 4—Cotton digestion by *Ruminococcus albus*

*Ruminococcus albus* was obtained from the American Type Culture Collection. It was cultured on Pseudomonas medium broth which contained the following (per liter of distilled $H_2O$):

Nitrilotriacetic acid: 1.91 g
$K_2HPO_4$: 8.71 g
$Na_2SO_4$: 0.57 g
$MgSO_4$: 0.25 g
$FeSO_4$: 0.5 mg
$Ca(NO_3)_2$: 0.5 mg
Agar: 1 g About 20 ml of the medium and 0.1 g cotton were added to each of 48 screw-cap tubes and sterilized. The tubes were then inoculated with 1 loopful of the microbe. To half of the tubes was added sufficient N-trichloromethylthio)-delta$^4$-tetrahydrophthalimide (Captan) to give a concentration of 10 micrograms per ml. The tubes were then sealed and incubated in a water bath for 70 hours at 40° C. At the end of the incubation period, the weight of undigested cotton was determined.

The Captan-treated tubes (average of 24) gave 22.7% cotton digestion. The control tubes (average of 24) gave 16.6% control.

EXAMPLE 5—Cotton digestion by *Bacteroides succinogenes* in rumen fluid

The rate of cotton digestion in the presence of N-trichloromethylthio-delta$^4$-tetrahydrophthalimide in sterilized rumen fluid with *Bacteroides succinogenes* was determined by a procedure identical to that of Example 1. After 70 hours incubation, the percent cotton digestion was 49.3%. In an untreated control run, the percent cotton digestion was 39.3%.

EXAMPLE 6—Rabbit feeding study

Ten rabbits were paired according to sex. One rabbit of each pair was given a basal ration and water ad lib. The other rabbit of each pair was fed the same basal ration, except that 1 mg of N-trichloromethylthio-delta$^4$-tetrahydrophthalimide (Captan) per 100 mg of body weight was also fed to the rabbit. The general health, daily feed, water consumed and weekly body weight of the rabbits was determined for a 5-week period. The initial body weight, weight gain, feed consumed and the feed consumed per gram of weight gain are tabulated in Tables IVa-IVd.

Table IVa

| | Initial Body Weights | |
|---|---|---|
| Pairs | Control (g) | Captan (g) |
| 1 | 1713 | 1572 |
| 2 | 1294 | 1507 |
| 3 | 1233 | 1787 |
| 4 | 1497 | 1527 |
| 5 | 1083 | 1168 |
| Total | 6820 | 7561 |
| Mean | 1564 | 1512 |

TABLE IVb

| | Gain in Body Weight | |
|---|---|---|
| Pairs | Control (g) | Captan (g) |
| 1 | 1120 | 1632 |
| 2 | 481 | 1226 |
| 3 | 361 | 1025 |
| 4 | 1019 | 1068 |
| 5 | 1280 | 1239 |
| Total | 4201 | 6173 |
| Mean | 840.2 | 1234 |

TABLE IVc

| | Feed Consumed | |
|---|---|---|
| Pairs | Control (g) | Captan (g) |
| 1 | 6252 | 7163 |
| 2 | 4959 | 7030 |
| 3 | 5032 | 5248 |
| 4 | 6973 | 7144 |
| 5 | 6970 | 7432 |
| Total | 30,246 | 36,024 |
| Mean | 6049.2 | 7204.8 |

TABLE IVd

| | Feed Consumed/Gram of Grain | |
|---|---|---|
| Pairs | Control (g) | Captan (g) |
| 1 | 5.58 | 4.38 |
| 2 | 10.31 | 5.73 |
| 3 | 14.11 | 7.80 |
| 4 | 6.84 | 6.74 |
| 5 | 5.71 | 6.05 |
| Total | 42.55 | 30.70 |
| Mean | 8.51 | 6.14 |

EXAMPLE 7—Cotton digestion by sewage bacteria

The rate of cotton digestion in the presence of N-trichloromethylthio-delta$^4$-tetrahydrophthalimide in a bacto-fluid thioglycolate nutrient broth by anaerobic sewage bacteria was determined by the following procedure.

A nutrient broth was prepared by reconstituting a fluid thioglycolate mixture (same composition as that described in Example 1) with supernatant water obtained from a mixture of distilled water (70%) and raw sewage (30%) taken from a sludge digestion tank of a commercial sewage treatment plant. Twenty milliliters of the nutrient broth solution containing 10 micrograms of the test compound and 100 mg of cotton were placed in screw-cap tubes (24 replicates). The tubes were inoculated with sewage bacteria by adding to the vial 0.5 ml of raw sewage sludge from the sewage treatment plant.

The tubes were closed and placed in a shaker, water bath maintained at 35° C. The caps were loosened every 2 hours for the first 6 hours of incubation and periodically thereafter at about 6-hour intervals to free accumulated gases of fermentation.

After 48 hours of incubation, the tubes were emptied on previously weighed filter paper. The filter paper was washed several times and dried to a constant weight. The weight of the undigested cotton was determined by difference.

The experiment (with 24 replicate tubes) was done with 6 different samples of sewage bacteria obtained every 2 weeks from the sewage treatment plant. The results for the 6 experiments are tabulated in Table V. The fermentation rate was increased by an average of 60% in the presence of the test compound.

TABLE V

| Level of Test Compound | Cellulose Fermentation by Sewage Bacteria | | | | | | |
|---|---|---|---|---|---|---|---|
| | 1 | 2 | 3 | 4 | 5 | 6 | Average |
| 0 | 55.0% | 52.6% | 59.6% | 56.3% | 57.6% | 55.1% | 55.6% |
| 10 micrograms | 94.3% | 94.3% | 97.1% | 89.3% | 95.4% | 96.3% | 94.4% |

What is claimed is:

1. A method for accelerating the rate of in vitro cellulose fermentation by cellulose-digesting microorganisms which comprises conducting said fermentation in the presence of a rate-accelerating amount of a compound of the formula

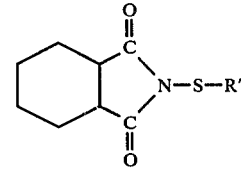

wherein R' is haloalkyl of 1 to 2 carbon atoms and 1 to 5 chloro or bromo groups and the carbocyclic ring has from 0 to 3 sites of olefinic unsaturation.

2. The method of claim 1 wherein the cellulose is cellulosic waste products.

3. The method of claim 2 wherein the microorganisms are sewage bacteria.

4. The method of claim 3 wherein R' is trichloromethyl or tetrachloroethyl.

5. The method of claim 4 wherein the compound is N-trichloromethylthio-delta$^4$-tetrahydrophthalimide or N-trichloromethylthiophthalimide.

6. The method of claim 4 wherein the compound is N-1,1,2,2-tetrachloroethylthio-delta$^4$-tetrahydrophthalimide or N-1,1,2,2-tetrachloroethylthiophthalimide.

* * * * *